United States Patent [19]

DeSantis et al.

[11] Patent Number: 5,173,507
[45] Date of Patent: Dec. 22, 1992

[54] PROSTAGLANDIN COMBINATIONS IN GLAUCOMA THERAPY

[75] Inventors: Louis M. DeSantis, Ft. Worth; Verney L. Sallee, Southlake, both of Tex.

[73] Assignee: Alcon Laboratories, Inc., Fort Worth, Tex.

[21] Appl. No.: 832,662

[22] Filed: Feb. 4, 1982

Related U.S. Application Data

[63] Continuation of Ser. No. 686,101, Apr. 16, 1991, abandoned, which is a continuation-in-part of Ser. No. 422,925, Oct. 17, 1989, abandoned, which is a continuation of Ser. No. 220,204, Jul. 18, 1988, abandoned.

[51] Int. Cl.$^5$ .................. A61K 31/215; A61K 31/19; A61K 31/557
[52] U.S. Cl. .................... 514/530; 514/573; 514/913
[58] Field of Search ............... 514/530, 573, 912, 913, 514/922

[56] References Cited

U.S. PATENT DOCUMENTS

| | | | |
|---|---|---|---|
| 4,029,681 | 6/1977 | Smith | 260/408 |
| 4,288,616 | 9/1981 | Sih | 562/503 |

FOREIGN PATENT DOCUMENTS 286903  3/1988  European Pat. Off. .

OTHER PUBLICATIONS

The Merck Index, 10th Edition (1983) p. 1135.
Kennedy et al., *Advances in Prostaglandin, Thromboxane and Leukotriene Research*, vol. II, (1983) pp. 327-332.
Dong et al, "Effects of Prostaglandins and Thromboxane Analogues on Bullock and Dog Iris Sphincter Preparations" The MacMillan Press, Ltd. 1982.
Sardar et al., *J. Pharm. and Exp. Therp* 247: 1064-1072 (1988).

*Primary Examiner*—Frederick E. Waddell
*Assistant Examiner*—Raymond J. Henley, III
*Attorney, Agent, or Firm*—Julie J. L. Cheng; Gregg C. Brown

[57] ABSTRACT

Disclosed is the use of combinations of the prostaglandins $PGF_{2\alpha}$ and $PGE_2$ and their respective derivatives, and pharmaceutically accceptable salts and esters thereof in the treatment of glaucoma and ocular hypertension. Also disclosed are ophthalmic, pharmaceutical compositions comprising said combinations.

3 Claims, No Drawings

PROSTAGLANDIN COMBINATIONS IN GLAUCOMA THERAPY

This application is a continuation of application Ser. No. 07/686,101, filed Apr. 16, 1991, now abandoned, which is a continuation-in-part of application Ser. No. 07/422,925 filed Oct. 17, 1989, now abandoned, which is a continuation of application Ser. No. 07/220,204 filed Jul. 18, 1988, now abandoned.

BACKGROUND OF THE INVENTION

This invention relates to the use of combinations of $PGF_{2\alpha}$ and $PGE_2$ prostaglandins and derivatives thereof in the treatment of glaucoma and ocular hypertension. $PGF_{2\alpha}$ and $PGE_2$ and their respective derivatives are represented by formulae (I) and (II) respectively:

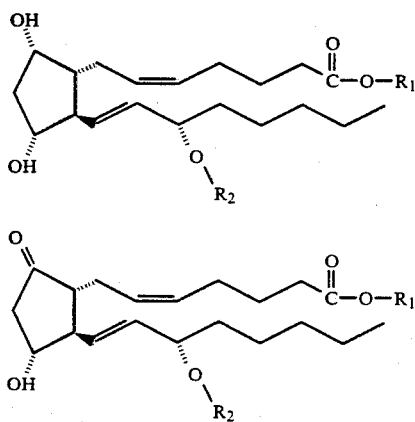

wherein $R_1$ is hydrogen, a cationic salt moiety, a pharmaceutically acceptable amine moiety or a pharmaceutically acceptable ester moiety derived from the corresponding alcohol; and $R_2$ is hydrogen or a pharmaceutically acceptable ester moiety derived from the corresponding carboxylic acid.

Natural prostaglandins are known to lower intraocular pressure (IOP) after topical ocular instillation, but can cause an inflammatory response. Many synthetic prostaglandins have been observed to lower intraocular pressure, but most such compounds also produce the described inflammatory response. It has been unexpectedly discovered that dosing with a combination of prostaglandins of formulae (I) and (II) produces a greater reduction of IOP than the equivalent dose of either compound given separately. In fact, as described in greater detail below, representative mixtures of prostaglandins (I) and (II) produce a profound and long lasting IOP decrease, even though the same dose of the $PGE_2$ component produced only a modest short decrease and twice the dose of $PGF_{2\alpha}$ produced no significant decrease in the primate model. Administration of both prostaglandins (I) and (II) is apparently necessary to produce the desired IOP lowering effect for glaucoma therapy. The requirement for two different prostaglandins to be present in the eye in order to achieve optimum IOP reduction has not been described before.

SUMMARY OF THE INVENTION

The extremely low dosage of the prostaglandin (PG) combination of the a present invention prevents or markedly decreases the local and/or systemic side effects seen with other glaucoma therapies—especially those based on PG therapy. A dosage of $PGF_{2\alpha}$ (I) adequate to lower IOP produces local irritation and discomfort. The combination of prostaglandins (I) and (II) allows this dosage to be decreased by 90% or more, thereby eliminating or s substantially reducing such irritation and discomfort.

Both $PGF_{2\alpha}$ and $PGE_2$ are naturally formed by the eye, and are normally present in aqueous humor as a combination. In addition, corneal tissue is capable of transforming exogenous $PGF_{2\alpha}$ into $PGE_2$ such that the $PGE_2$ concentration in aqueous humor is increased following topical ocular dosing with $PGF_{2\alpha}$. It is therefore reasonable to propose that the potent IOP lowering effect of the present PG combinations is somehow attributable to the combination of $PGF_{2\alpha}$, or derivatives of formula (I), with $PGE_2$, or derivatives of formula (II). The limited response to dosage with $PGF_{2\alpha}$ alone is consistent with this proposed explanation. Although the mechanism for the observed synergism is unknown, it is clear that dosage with an optimum combination of $PGF_\alpha$ and $PGE_2$ will allow a more potent reduction of intraocular pressure without the side-effects produced by treatment with an adequate dose of a single component.

DETAILED DESCRIPTION OF THE INVENTION

The compounds of the present invention are known. See, for example, *The Merck Index*, 10th Edition (1983), which is incorporated herein by reference to the extent that it describes the preparation and known pharmacological profiles of $PGF_{2\alpha}$ and $PGE_2$ and the derivatives of formulae (I) and (II) described below:

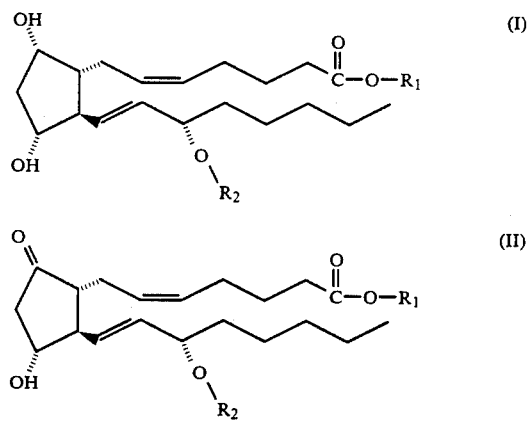

In the foregoing formulae (I) and (II), $R_1$ is hydrogen, a cationic salt moiety, a pharmaceutically acceptable amine moiety or a pharmaceutically acceptable ester moiety derived from the corresponding alcohol; and $R_2$ is hydrogen or a pharmaceutically acceptable ester moiety derived from the corresponding carboxylic acid. As used herein, the term "pharmaceutically acceptable salts and esters" means esters and salts of these compounds which have the same general pharmacological properties as the acid form from which they are derived, and which are acceptable from a toxicity viewpoint. Specifically included by this term are salts and esters of the type disclosed in U.S. Pat. No. 4,029,681 (Jun. 19, 1977) and in U.S. Pat. No. 4,288,616 (Sep. 8, 1981), the disclosures of which are hereby incorporated in the present specification by reference. Thus, the compounds covered by the above general formulae include the free acid ($R_1=H$) and alcohol ($R_2=H$), alkali and alkaline earth metal salts (e.g., Na, K, Ca, and Mg), ammonium and amine salts, and esters ($R_1$=alkyl, or $R_2$=acyl). Preferred salts are those involving alkali and alkaline earth metal cations, particularly sodium and potassium, and amine salts, especially tris(hydroxymethyl)aminomethane salts. Preferred esters are $C_1$-$C_{12}$ alkyl esters, particularly straight or branched $C_1$-$C_6$ alkyl esters, especially methyl, ethyl, isopropyl, cyclopropyl, cyclopropyl methyl, butyl, cyclobutyl, isobutyl, butyl or pentyl.

Alkali metal salts and alkaline earth metal salts of the acid form of (I) and (II) may be formed conventionally. The alcohol and/or acid or salt may be subsequently esterified with the appropriate acid and/or alcohol, e.g., a $C_1$-$C_3$ alkyl alcohol, to yield the final ester product embodiment of (I) and (II) according to known procedures.

In a similar manner, other esterifications may be effected as is known in the art employing other low alkyl, cycloalkyl, cycloalkyalkyl, aryl, or aryalkyl alcohols and/or acids such as isopropanol, cyclopropanol, cyclopropylmethanol, or phenyl or benzyl alcohol. Since such esterification reactions are well known, they are not further described here.

The prostaglandins (I) and (II) are combined in a molar ratio in the range of 0.1:1.0 to 1000:1, respectively. The preferred range is 4:1 to 20:1. Most preferred is a molar ratio of 10:1.

The combinations of compounds of formulae (I) and (II) are useful in lowering intraocular pressure and thus are useful in the treatment of glaucoma. As compared with therapeutically effective dosages of the individual components, the combinations produce significantly fewer unwanted side effects such as marked vasoconstriction or vasodilation of the vessels of the sclera, painful stinging and intraocular inflammation.

The combinations are preferably administered topically. The dosage range is about 0.00001 to about 1.0 mg/eye and preferably about 0.0001 mg/eye; wherein the cited mass figures represent the sum of the two components, (I) and (II). The combinations of the present invention can be administered as solutions, suspensions, or emulsions (dispersions) in a suitable ophthalmic vehicle.

In forming compositions for topical administration, the mixtures are generally formulated as between about 0.0001 to about 2.0 percent by weight (wt. %) solutions in water at a pH between 4.5 to 8.0 (figures relate to combined presence of (I) and (II)). The mixtures are preferably formulated as between about 0.0001 to about 0.1 wt. % and, most preferably, about 0.01 wt. %. While the precise regimen is left to the discretion of the clinician, it is recommended that the resulting solution be topically applied by placing one drop in each eye two times a day.

Other ingredients which may be desirable to use in the ophthalmic preparations of the present invention include preservatives, co-solvents and viscosity building agents.

Antimicrobial Preservatives

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level of from 0.001% to 1.0% by weight.

Co-Solvents

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; cyclodextrin; or other agents known to those skilled in the art. Such co-solvents are typically employed at a level of from 0.01% to 2% by weight.

Viscosity Agents

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art. Such agents are typically employed at a level of from 0.01% to 2% by weight.

The following examples are representative pharmaceutical compositions of the invention for topical use in lowering of intraocular pressure.

EXAMPLE A

| Ingredient | Percentage by Weight |
| --- | --- |
| (II): $R_1 = CH_3$; $R_2 = H$ | 0.001 |
| (I): $R_1 = CH(CH_3)_2$; $R_2 = H$ | 0.02 |
| Benzalkonium chloride | 0.01 |
| Polysorbate 80 | 0.05 |
| Sodium acetate | 0.07 |
| Sodium chloride | 0.6 |
| Hydroxypropyl methyl cellulose | 0.5 |
| Hydrochloric acid and/or sodium hydroxide | to adjust pH |
| Purified water | q. s. to 100% |

EXAMPLE B

| Ingredient | Percentage by Weight |
| --- | --- |
| (II): $R_1 = CH_3$; $R_2 = H$ | 0.0005 |
| (I): $R_1 = CH(CH_3)_2$; $R_2 = H$ | 0.005 |
| Benzalkonium chloride | 0.01 |
| Pluronic P-84 | 0.5 |
| Dried sodium phosphate | 0.01 |
| Sodium biphosphate | 0.07 |
| Sodium chloride | 0.18 |
| Sodium hydroxide and/or hydrochloric acid | to adjust pH |
| Purified water | q. s. to 100% |

EXAMPLE C

| Ingredient | Percentage by Weight |
| --- | --- |
| (II): $R_1 = CH_3$; $R_2 = H$ | 0.00025 |
| (I): $R_1 = CH(CH_3)_2$; $R_2 = H$ | 0.001 |

-continued

| Ingredient | Percentage by Weight |
| --- | --- |
| Chlorobutanol | 0.5 |
| Sodium acetate | 0.14 |
| Disodium edetate | 0.01 |
| Sodium chloride | 0.52 |
| Hydrochloric acid and/or sodium hydroxide | to adjust pH |
| Polyvinyl alcohol | 1.0 |
| Purified water | q. s. to 100% |

EXAMPLE D

| Ingredient | Percentage by Weight |
| --- | --- |
| (II): $R_1 = CH_3$; $R_2 = H$ | 0.0002 |
| (I): $R_1 = CH(CH_3)_2$; $R_2 = H$ | 0.002 |
| Benzalkonium chloride | 0.01 |
| Dextran 70 | 0.1 |
| Disodium edetate | 0.05 |
| Potassium chloride | 0.12 |
| Sodium chloride | 0.77 |
| Hydroxypropyl methyl cellulose | 0.3 |
| Hydrochloric acid and/or sodium hydroxide | to adjust pH |
| Purified water | q. s. to 100% |

EXAMPLE E

| Ingredient | Percentage by Weight |
| --- | --- |
| (II): $R_1 = CH_3$; $R_2 = H$ | 0.0001 |
| (I): $R_1 = CH(CH_3)_2$; $R_2 = H$ | 0.001 |
| Benzalkonium chloride | 0.01 |
| Dextran 70 | 0.1 |
| Disodium edetate | 0.05 |
| Potassium chloride | 0.12 |
| Sodium chloride | 0.77 |
| Hydroxypropyl methyl cellulose | 0.3 |
| Hydrochloric acid and/or sodium hydroxide | to adjust pH |
| Purified water | q. s. to 100% |

EXAMPLE F

| Ingredient | Percentage by Weight |
| --- | --- |
| (II): $R_1$ = isobutyl; $R_2 = H$ | 0.0001 |
| (I): $R_1 = CH_2CH_3$; $R_2 = H$ | 0.0005 |
| Benzalkonium chloride | 0.01 |
| Dextran 70 | 0.1 |
| Disodium edetate | 0.05 |
| Potassium chloride | 0.12 |
| Sodium chloride | 0.77 |

-continued

| Ingredient | Percentage by Weight |
| --- | --- |
| Hydroxypropyl methyl cellulose | 0.3 |
| Hydrochloric acid and/or sodium hydroxide | to adjust pH |
| Purified water | q. s. to 100% |

The invention has been described herein by reference to certain preferred embodiments. However, as obvious variations thereon will become apparent to those skilled in the art, the invention is not to be considered as limited thereto.

What is claimed is:

1. A method of treating glaucoma and ocular hypertension which comprises topically administering to an affected eye a pharmaceutical composition comprising a combination of a compound of formula (I) and a compound of formula (II):

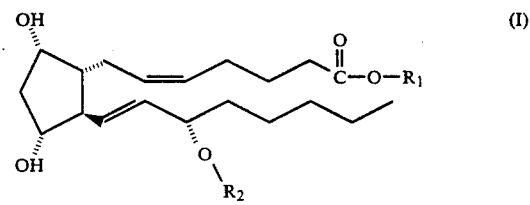

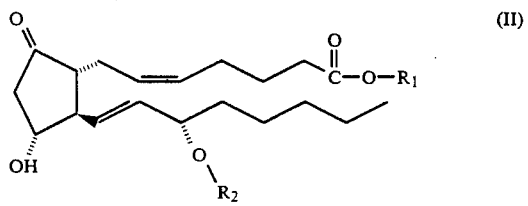

wherein:
$R_1$ = hydrogen, or a pharmaceutically acceptable salt or ester moiety; and
$R_2$ = hydrogen, or a pharmaceutically acceptable ester moiety;

wherein the concentration of a compound of formula (I) is in the range of 0.001 to 0.002 wt % and the concentration of a compound of formula (II) is in the range of 0.0001 to 0.0002 wt %; and wherein the molar ratio of (I):(II) is in the range of 4:1 to 20:1.

2. The method of claim 1, wherein the molar ratio of (I):(II) is 10:1.

3. The method of claim 1, wherein $R_1$ is isopropyl and $R_2$ is hydrogen in the compound of formula (I) and $R_1$ is methyl and $R_2$ is hydrogen in the compound of formula (II).

* * * * *